(12) United States Patent
Maryanoff et al.

(10) Patent No.: US 6,740,657 B2
(45) Date of Patent: May 25, 2004

(54) AMINOMETHYL-PYRROLOQUINAZOLINE COMPOUNDS AS THROMBIN RECEPTOR ANTAGONISTS

(75) Inventors: Bruce E. Maryanoff, Forest Grove, PA (US); Han-Cheng Zhang, Lansdale, PA (US); David F. McComsey, Warminster, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/059,707

(22) Filed: Jan. 29, 2002

(65) Prior Publication Data

US 2002/0160963 A1 Oct. 31, 2002

Related U.S. Application Data

(60) Provisional application No. 60/270,988, filed on Feb. 23, 2001.

(51) Int. Cl.$^7$ ............... A61K 38/05; A61K 31/519; C07D 487/04
(52) U.S. Cl. ............... 514/267; 514/19; 544/250
(58) Field of Search ............... 514/267, 19; 544/250; 562/433, 516, 553

(56) References Cited

U.S. PATENT DOCUMENTS

| | | | | |
|---|---|---|---|---|
| 4,118,561 | A | 10/1978 | Ledig | 542/470 |
| 4,208,520 | A | 6/1980 | Ledig, deceased et al. | 544/250 |
| 4,451,466 | A | 5/1984 | Horne et al. | 424/251 |
| 2003/0105081 | A1 * | 6/2003 | Yohannes et al. | 514/220 |

FOREIGN PATENT DOCUMENTS

WO    WO 93/10119 A1    5/1993

OTHER PUBLICATIONS

Ho–Sam Ahn, "Structure–Activity Relationships of Pyrroloquinazolines as Thrombin Receptor Antagonists", Bioorganic & Medicinal Chemistry Letters 9, (1999) pp. 2073–2078.

T.–K. Vu, "Molecular Cloning of a Functional Thrombin Receptor Reveals a Novel Proteolytic Mechanism of Receptor Activation", *Cell* 1991, 64, 1057.

S. Nystedt, "Molecular cloning of a potential proteinase activated receptor", *Proc. Natl. Acad. Sci USA* 1994, 91, 9208.

H. Ishihara, "Protease–activated receptor 3 in a second thrombin receptor in humans", *Nature* 1997, 386, 502.

W.–F. Xu, "Cloning and characterization of human protease–activated receptor 4", *Proc. Natl. Acad. Sci USA* 1998, 95, 6642.

J. J. Cook, "An Antibody Against the Exosite of the Cloned Thrombin Recepotr Inhibits Experimental Arterial Thrombosis in the African Green Monkey", *Circulation* 1995, 91, 2961.

Y. Sugama, "Thrombin–induced Expression of Endothelial P–Selectin and Intercellular Adhesion Molecule–1: A Mechanism for Stabilizing Neutorphil Adhesion", J. Cell Biol. 1992, 119, 935.

D. T. Hung, "Thrombin–induced Events in Non–Platelet Cells Are Mediated by the Unique Proteolytic Mechanism Establihshed for the Cloned Platelet Thrombin Recepotr", *J. Cell Biol.* 1992, 116, 827.

D. N. Tatakis, "Thrombin Effects on Osteoblastic Cells II. Structure–Function Relationships" *Biochem. Biophys. Res. Commun.* 1991, 174, 181.

K. Jalink, "Thrombin Receptor Activation Causes Rapid Neural Cell Rounding and Neurite Retraction Independent of Classic Second Messengers", *J. Cell Biol.* 1992, 118, 411.

C.L.A. Jones, "Response of a human megarkaryocytic cell line to thrombin: Increase in intracellular free calcium and mitogen release", Biochim. Biophys. Acta, Vol 1136 (1992) pp. 272–282.

International Search Report for PCT/US02/02489 dated Aug. 21, 2002.

* cited by examiner

*Primary Examiner*—Richard L. Raymond
*Assistant Examiner*—Tamthom N. Truong

(57) ABSTRACT

The invention is directed to novel aminomethyl-pyrroloquinazoline compounds and pharmaceutical compositions thereof which are useful thrombin receptor or PAR-1 antagonists, methods for production thereof and methods for treating thrombin or PAR-1 mediated disorders.

27 Claims, No Drawings

AMINOMETHYL-PYRROLOQUINAZOLINE COMPOUNDS AS THROMBIN RECEPTOR ANTAGONISTS

This applications claims benefit of provisional patent application 60/270,988 filed on Feb. 23, 2001, which is incorporated herein by reference.

FIELD OF THE INVENTION

This invention relates to certain novel compounds, their synthesis and their use for the treatment of thrombin receptor mediated diseases. More particularly, this invention relates to aminomethyl-pyrroloquinazoline compounds and pharmaceutical compositions thereof useful as thrombin receptor antagonists, methods for production thereof and methods for treating thrombin receptor mediated disorders.

BACKGROUND OF THE INVENTION

Thrombin is an important serine protease in hemostasis and thrombosis. One of the key actions of thrombin is cellular modulation via receptor activation. A functional human thrombin receptor (PAR-1), cloned by Coughlin in 1991 (T.-K. Vu, *Cell* 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence, which has an SFLLRN (Ser-Phe-Leu-Leu-Arg-Asn) N-terminus acting as a tethered ligand to recognize a site on the receptor, can trigger activation and signal transduction leading to platelet aggregation. Since 1991, three other protease-activated receptors with extensive homology to the thrombin receptor, "PAR-2" (S. Nystedt, *Proc. Nat. Acad. Sci USA* 1994, 91, 9208), "PAR-3" (H. Ishihara, *Nature* 1997, 386, 502), and "PAR-4" (W.-F. Xu, *Proc. Natl. Acad. Sci USA* 1998, 95, 6642), have been cloned. The thrombin PAR-1 specific antibody-induced blockade of the platelet thrombin receptor has shown efficacy against arterial thrombosis in vivo (J. J. Cook *Circulation* 1995, 91, 2961). Hence, antagonists of the thrombin PAR-1 are useful to block these protease-activated receptors and, as such, may be used to treat platelet mediated thrombotic disorders such as myocardial infarction, stroke, restenosis, angina, atherosclerosis and ischemic conditions.

The thrombin PAR-1 has also been identified on other cell types: endothelial, fibroblast, renal, osteosarcoma, smooth muscle, myocytes, tumor, and neuronal/glia. Thrombin activation of endothelial cells upregulates P-selectin to induce polymorphonuclear leukocyte adhesion—an inflammatory response of the vessel wall (Y. Sugama, *J. Cell Biol.* 1992,119, 935). In fibroblasts, PAR-1 activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174,181). Thrombin has been implicated in the regulation and retraction of neurons (K. Jalink, *J. Cell. Biol.* 1992, 118, 411). Therefore, in this context, thrombin receptor antagonist compounds, particularly PAR-1 antagonists, may also be useful against inflammation, osteoporosis, cancer, neurodegenerative disorders, hypertension, heart failure, arrhythmia or glomerulonephritis.

The structure activity relationships of pyrroloquinazoline compounds as small molecule inhibitors of the intramolecular ligand of the thrombin receptor have been reported (D. A. Burnett, et al., *Bioorg. Med. Chem. Lett.,* 1999, 2073–2077), disclosing pyrroloquinazoline compounds of the general formula:

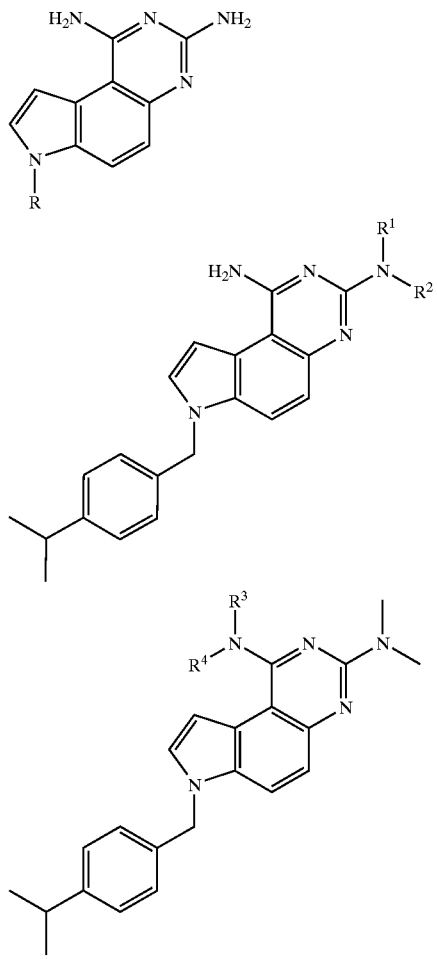

wherein R is selected from 4-(i-Pr)benzyl, 4-(t-Bu)benzyl, 6-(Me)naphthalen-2-ylmethyl, 4-(OEt)benzyl, 4-(Et)benzyl, 4-(SMe)benzyl, 4-(ethenyl)benzyl; $NR^1R^2$ is selected from methylamino, dimethylamino, ethylamino, ethanolamino, N-cyclopropylamino, N-methyl-N-cyclopropylamino, 1-piperidinyl, 2-1,2,3,4-tetrahydro-isoquinoline or 1-piperazinyl; and, $NR^3R^4$ is selected from amino, methylamino or dimethylamino.

U.S. Pat. No. 4,118,561 to Ledig discloses 7-(substituted) and 7,8-disubstituted pyrrolo[3,2-f]quinazoline-1,3-diamines having anti-bacterial activity of the general formula:

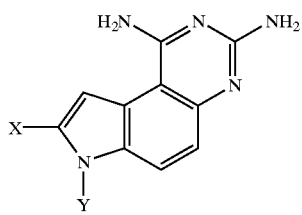

wherein (a) X is hydrogen and Y is —CH₂R or —R¹ wherein R is hydrogen; methyl; ethyl; n-propyl; i-propyl; n-butyl; i-butyl; n-pentyl; n-hexyl; 2-methyl-1-propenyl; cyclobutyl; cyclopentyl; cyclohexyl; 2-phenylethyl; 2-phenylvinyl; phenyl; phenyl monosubstituted in the 2-, 3-, or 4-position by chlorine, bromine, iodine, fluorine, trifluoromethyl, methyl, ethyl, n-propyl, i-propyl, n-butyl, i-butyl, t-butyl, methoxy, ethoxy, n-propoxy, trifluoromethoxy, cyano, methylsulfonyl, acetyl, propionyl, methylthio, ethylthio, carbethoxy, carboxyl, sodium carboxy, or potassium carboxy; phenyl monosubstituted in the 3-position by amino or nitro; phenyl disubstituted in the 2,3-, 2,4-, 2,5-, 2,6-, 3,4- or 3,5- positions by methyl, ethyl, n-propyl, methoxy, ethoxy, n-propoxy, chlorine, bromine, iodine or fluorine; phenyl trisubstituted in the 2,4,6- or 3,4,5-positions by methyl, ethyl, methoxy, or ethoxy; 2,3,5,6-tetramethylphenyl; 3,4-(methylenedioxy)phenyl; 1-naphthalenyl; 2-naphthalenyl, 2-methyl-1-naphthalentyl; 1-bromo-2-naphthalentyl; 2-pyrindinyl; 3-pyrindinyl; 4-pyrindinyl; 2-quinolinyl; 8-quinolinyl; 2-thienyl; 3-thienyl; 4-thiazolyl, 3,5-dimethyl-4-isoxazolyl; tetrahydro-2-furanyl; or benzo[b]thien-3-yl; and R¹ is hydrogen; phenyl monosubstituted in the 2- or 4-position by amino, nitro, cyano, acetyl, propionyl, methylsulfonyl, trifluoromethyl or carbethoxy; 2,4-dinitrophenyl; 2,4-diaminophenyl; 2-cyano-4-nitrophenyl; 2-cyano-4-aminophenyl; 3-methyl-4-nitrophenyl; 3-methyl-4-aminophenyl; 2-trifluoromethyl-4-nitrophenyl; 2-trifluoromethyl-4-aminophenyl; 2-thiazolyl; 2-pyrindinyl; 5-nitro-2-pyrindinyl; 2-pyrimidinyl; 2-pyrazinyl; 2-quinolinyl; 4-quinolinyl; 4-methyl-2-quinolinyl; 7-chloro-4-quinolinyl; 7-trifluoromethyl-4-quinolinyl; 2-methyl-4-quinolinyl; 3-methyl-2-quinoxalinyl; 2-phenyl-4-quinolinyl; or benzothiazolyl; 5-amino-2-pyrindinyl; and (b) X is methyl, phenyl, or chlorine, and Y is hydrogen, methyl, benzyl, 3-cyanobenzyl, 4-cyanobenzyl, or 2,5-dimethylbenzyl; provided that when X is phenyl, Y may only be hydrogen or methyl, and when X is chlorine, Y may only be benzyl.

The aminomethyl-pyrroloquinazoline compounds of the present invention have not been heretofore disclosed as thrombin receptor antagonists. Accordingly, it is an object of the present invention to provide aminomethyl-pyrroloquinazoline compounds useful as thrombin receptor antagonists, particularly as PAR-1 antagonists. It is another object of the invention to provide methods for producing the instant aminomethyl-pyrroloquinazoline compounds. It is a further object of the invention to provide methods for treating thrombin receptor mediated disorders, particularly PAR-1 mediated disorders including, but not limited to, inflammation, osteoporosis, hypertension, angina, atherosclerosis, thrombosis, restenosis, arrhythmia, myocardial infarction, heart failure, stroke, ischemic conditions, glomerulonephritis, cancer and neurodegenerative disorders.

SUMMARY OF THE INVENTION

The present invention is directed to structurally novel aminomethyl-pyrroloquinazoline compounds of Formula (I):

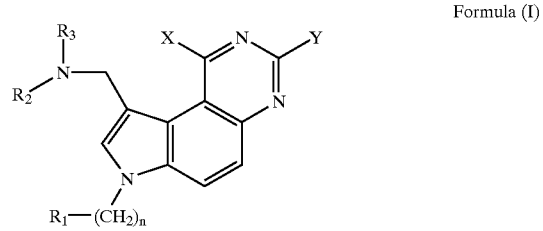

Formula (I)

wherein:

$R_1$ is selected from the group consisting of aryl, heteroaryl and $C_3$–$C_8$ cycloalkyl optionally substituted with one to five substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heteroaryl, amino, amido, amidino, guanidino, hydroxy, nitro and cyano;

$R_2$ and $R_3$ are independently selected from the group consisting of hydrogen, $C_1$–$C_8$ alkyl, $C_2$–$C_8$ alkenyl, $C_2$–$C_8$ alkynyl, $C_3$–$C_8$ cycloalkyl and aryl($C_1$–$C_8$)alkyl; alternatively, when independently selected from the group consisting of $C_1$–$C_8$ alkyl and $C_2$–$C_8$ alkenyl, $R_2$ and $R_3$ may, together with the nitrogen to which they are attached, form a saturated or partially saturated 4 to 6 membered heterocyclyl ring;

n is an integer selected from 0, 1, 2 or 3;

X is selected from the group consisting of hydrogen, —$OR_4$, —$NH_2$, —$NHR_4$ and —$NR_4R_5$;

$R_4$ and $R_5$ are independently selected from the group consisting of $C_1$–$C_8$alkyl, $C_3$–$C_8$ cycloalkyl and aryl($C_1$–$C_8$) alkyl;

Y is selected from the group consisting of halogen, —$NH_2$, —$NHR_6$, —$NR_6R_7$, —$A_1$—$NH_2$, —$A_1$—$NHR_6$, —$A_1$—$NR_6R_7$, —$A_1$—$A_2$—$NH_2$, —$A_1$—$A_2$—$NHR_6$ and —$A_1$—$A_2$—$NR_6R_7$;

$R_6$ and $R_7$ are independently selected from the group consisting of $C_1$–$C_8$alkyl, $C_3$–$C_8$ cycloalkyl and aryl($C_1$–$C_8$) alkyl; and, $A_1$ and $A_2$ are independently selected from the L-amino acid residue group consisting of arginine, homoarginine, 2,4-diaminobutyric acid, lysine, ornithine, histidine, phenylalanine, homophenylalanine, naphthylalanine, cyclohexylalanine, tryptophan and tyrosine optionally substituted with one to three substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heterocyclyl, amino, amido, amidino, guanidino, hydroxy, nitro and cyano;

and pharmaceutically acceptable salts thereof.

In an embodiment of the invention, the instant aminomethyl-pyrroloquinazoline compounds are useful thrombin receptor antagonists; in particular, useful PAR-1 antagonists.

The present invention also embodies methods for producing the instant aminomethyl-pyrroloquinazoline compounds. Illustrative of the invention is a pharmaceutical composition comprising a pharmaceutically acceptable carrier and any of the compounds described above. Another illustration of the invention is a pharmaceutical composition made by mixing any of the compounds described above and a pharmaceutically acceptable carrier. Also illustrative of the invention is a process for making a pharmaceutical composition comprising mixing any of the compounds described above and a pharmaceutically acceptable carrier. The present invention is intended to include the use of any of the compounds described above for the preparation of a medicament for treating a thrombin or PAR-1 mediated disorder.

A further embodiment of the invention is a method for treating thrombin mediated disorders (preferably, platelet-mediated thrombotic or vaso-occlusive disorder in a subject in need thereof); in particular, a method for treating PAR-1 mediated disorders including, but not limited to, inflammation, osteoporosis, hypertension, unstable angina, atherosclerosis, arterial and/or venous thrombosis, restenosis, arrhythmia, acute myocardial infarction, heart failure, stroke, ischemic conditions, reocclusion following thrombolytic therapy and/or angioplasty, glomerulonephritis, cancer or neurodegenerative disorders.

DETAILED DESCRIPTION OF THE INVENTION

We have discovered a structurally novel class of aminomethyl-pyrroloquinazoline compounds of Formula (I) which are unlike those known in the art in that an aminomethyl group has been positioned on the pyrrolo portion of the pyrroloquinazoline scaffold. Moreover, we have discovered that the instant aminomethyl-pyrroloquinazoline compounds are thrombin receptor antagonists; and, in particular, that the instant compounds are PAR-1 antagonists.

Embodiments of the present invention include those compounds wherein, preferably, $R_1$ is selected from the group consisting of aryl and heteroaryl optionally substituted with one to five substituents independently selected from the group consisting of halogen, $C_1$–$C_4$ alkyl, $C_1$–$C_4$ alkoxy, amino, amido, amidino, guanidino, hydroxy, nitro and cyano.

More preferably, $R_1$ is selected from aryl optionally substituted with one to five substituents independently selected from the group consisting of halogen, $C_1$–$C_4$ alkyl, $C_1$–$C_4$ alkoxy, amino, amido, amidino, guanidino, hydroxy, nitro and cyano.

Most preferably, $R_1$ is selected from phenyl substituted with two substituents independently selected from halogen.

Embodiments of the present invention include those compounds wherein, preferably, $R_2$ and $R_3$ are independently selected from $C_1$–$C_4$ alkyl; alternatively, $R_2$ and $R_3$ may, together with the nitrogen to which they are attached, form a saturated 5 or 6 membered heterocyclyl ring.

More preferably, $R_2$ and $R_3$ are independently selected from the group consisting of methyl, ethyl and propyl; alternatively, $R_2$ and $R_3$ may, together with the nitrogen to which they are attached, form a saturated heterocyclyl ring selected from the group consisting of pyrrolidinyl and piperidinyl.

Most preferably, $R_2$ and $R_3$ are selected from methyl; alternatively, $R_2$ and $R_3$ may, together with the nitrogen to which they are attached, form a saturated heterocyclyl ring selected from pyrrolidinyl.

Embodiments of the present invention include those compounds wherein, preferably, n is 1.

An embodiment of the present invention includes those compounds wherein, preferably, X is selected from the group consisting of hydrogen, —$OR_4$, —$NH_2$, —$NHR_4$ and —$NR_4R_5$. More preferably, X is selected from the group consisting of hydrogen, —$OR_4$ and —$NH_2$. Most preferably, X is selected from —$NH_2$.

An embodiment of the present invention includes those compounds wherein, preferably, $R_4$ and $R_5$ are selected from $C_1$–$C_8$alkyl. More preferably, $R_4$ is selected from the group consisting of methyl, ethyl and propyl. Most preferably, $R_4$ is methyl.

An embodiment of the present invention includes those compounds wherein, preferably, Y is selected from the group consisting of halogen, —$NHR_6$, —$NR_6R_7$ and —$A_1$—$A_2$—$NHR_6$. More preferably, Y is selected from the group consisting of chlorine, —$NHR_6$, —$NR_6R_7$ and —$A_1$—$A_2$—$NHR_6$. Most preferably, Y is selected from the group consisting of —$NHR_6$ and —$A_1$—$A_2$—$NHR_6$.

An embodiment of the present invention includes those compounds wherein, preferably, $R_6$ and $R_7$ are independently selected from the group consisting of methyl, ethyl, propyl, cyclopropyl, cyclopentyl, cyclohexyl, benzyl, phenethyl and phenylpropyl. More preferably, $R_6$ and $R_7$ are independently selected from the group consisting of methyl, cyclopropyl and benzyl. Most preferably, $R_6$ is selected from the group consisting of cyclopropyl and benzyl.

An embodiment of the present invention includes those compounds wherein, preferably, $A_1$ and $A_2$ are independently selected from the L-amino acid residue group consisting of 2,4-diaminobutyric acid and phenylalanine.

As listed in Table 1, exemplifying the invention is a compound of Formula (I) selected from:

TABLE 1

| No. | Compound Name |
|---|---|
| 1 | $N^3$-cyclopropyl-7-[(2,6-dichlorophenyl)methyl]-9-[(dimethylamino)methyl]-7H-pyrrolo[3,2-f]quinazoline-1,3-diamine; |
| 2 | α-[[1-amino-7-[(2,6-dichlorophenyl)methyl]-9-[(dimethylamino)methyl]-7H-pyrrolo[3,2-f]quinazolin-3-yl]amino]-N-[(1S)-3-amino-1-[[(phenylmethyl)amino]carbonyl]propyl]-, ($α^1$S)-benzenepropanamide; |
| 3 | 7-[(2,6-dichlorophenyl)methyl]-9-[(dimethylamino)methyl]-$N^3,N^3$-dimethyl-7H-pyrrolo[3,2-f]quinazoline-1,3-diamine; |
| 4 | 3-(cyclopropylamino)-7-[(2,6-dichlorophenyl)methyl]-N,N-dimethyl-7H-pyrrolo[3,2-f]quinazoline-9-methanamine; |
| 5 | 3-chloro-7-[(2,6-dichlorophenyl)methyl]-9-(1-pyrrolidinylmethyl)-7H-pyrrolo[3,2-f]quinazolin-1-amine; |
| 6 | 3-chloro-7-[(2,6-dichlorophenyl)methyl]-1-methoxy-N,N-dimethyl-7H-pyrrolo[3,2-f]quinazoline-9-methanamine; or, |
| 7 | 1-amino-3-chloro-7-[(2,6-dichlorophenyl)methyl]-N,N-dimethyl-7H-pyrrolo[3,2-f]quinazoline-9-methanamine; | and pharmaceutically acceptable salts thereof.

Representative Chemical Abstracts Service (CAS) Index-like names for the compounds of the present invention were derived using the ACD/LABS SOFTWARE™ Index Name Pro Version 4.5 nomenclature software program provided by Advanced Chemistry Development, Inc., Toronto, Ontario, Canada.

As listed in Table 2, the invention is exemplified by a compound of Formula (Ia):

TABLE 2

Formula (Ia)

[Chemical structure diagram showing a tricyclic indole-pyrimidine compound with substituents $R_3$, $R_2$, N, X, Y, Cl, Cl]

wherein X, Y, $R_2$ and $R_3$ are dependently selected from the group consisting of:

| Cpd | X | Y | $R_2$, $R_3$ |
|---|---|---|---|
| 1 | $NH_2$ | NH-c-$C_3H_5$ | $CH_3$, $CH_3$; |
| 2 | $NH_2$ | -Phe-Dbu-Bzl | $CH_3$, $CH_3$; |
| 3 | $NH_2$ | $N(CH_3)_2$ | $CH_3$, $CH_3$; |
| 4 | H | NH-c-$C_3H_5$ | $CH_3$, $CH_3$; |
| 5 | $NH_2$ | Cl | —$(CH_2)_4$—; |
| 6 | $OCH_3$ | Cl | $CH_3$, $CH_3$; and, |
| 7 | $NH_2$ | Cl | $CH_3$, $CH_3$; | and pharmaceutically acceptable salts thereof.

As listed in Table 3, the invention includes preferred compounds of Formula (Ia) wherein X, Y, $R_2$ and $R_3$ are dependently selected from the group consisting of:

TABLE 3

| Cpd | X | Y | $R_2$, $R_3$ |
|---|---|---|---|
| 1 | $NH_2$ | NH-c-$C_3H_5$ | $CH_3$, $CH_3$; and, |
| 2 | $NH_2$ | -Phe-Dbu-Bzl | $CH_3$, $CH_3$; | and pharmaceutically acceptable salts thereof.

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "alkyl" refers to straight and branched-chain alkyl radical groups; similarly, alkenyl and alkynyl radicals include straight and branched chains having 2 to 8 carbon atoms or any number within this range; wherein one or two double or triple bonds are formed in the chain between adjacent members. The term "alkoxy" refers to O-alkyl groups where alkyl is as defined supra. The term cycloalkyl refers to a cyclic alkyl ring of three to eight carbon atom members. Examples of such cyclic alkyl rings include cyclopropyl, cyclopentyl, cyclohexyl or cycloheptyl.

The term "heterocyclyl" as used herein refers to an optionally substituted, stable, saturated or partially unsaturated 3 to 10 membered monocyclic or benzofused bicyclic ring system which consists of carbon atoms and from one to three heteroatoms selected from N, O or S. The heterocyclyl group may be attached at any heteroatom or carbon atom which results in the creation of a stable structure and, accordingly, may be further attached to, for example, alkyl or alkoxy chains. When a hetercyclo group is further substituted, one or both rings may be optionally substituted with one to five substituents attached at any heteroatom or carbon atom which results in the creation of a stable structure.

The term aryl refers to a single aromatic ring of six carbon members or a bicyclic aromatic ring of ten carbon members. Examples of such aryl rings include phenyl and naphthyl.

The term heteroaryl refers to an aromatic monocyclic ring of five or six members or benzofused bicyclic ring system wherein at least one member is a heteroatom. Suitable heteroatoms include nitrogen, oxygen or sulfur. In the case of five-membered rings, the heteroaryl ring contains one member of nitrogen, oxygen or sulfur and, in addition, may contain up to two additional nitrogens. In the case of six-membered rings, the heteroaryl ring may contain from one to three nitrogen atoms. For the case wherein the six member ring has three nitrogens, at most two nitrogen atoms are adjacent. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl.

The term "arylalkyl" refers to an alkyl group substituted at the terminal carbon with an aryl group (e.g., benzyl, phenethyl). The term "halogen" refers to a iodine, bromine, chlorine or fluorine atom.

Whenever the term "alkyl" or "aryl" or either of their prefix roots appear in a name of a substituent (e.g., aryl $(C_1-C_4)$alkyl) it shall be interpreted as including those limitations given above for "alkyl" and "aryl." Designated numbers of carbon atoms (e.g., $C_1-C_6$) shall refer independently to the number of carbon atoms in an alkyl or cycloalkyl moiety or to the alkyl portion of a larger substituent in which alkyl appears as its prefix root.

Under standard nomenclature rules used throughout this disclosure, the terminal portion of the designated side chain is described first followed by the adjacent functionality toward the point of attachment. Thus, for example, a "phenyl$C_{1-6}$alkylamido$C_{1-6}$alkyl" substituent refers to a group of the formula:

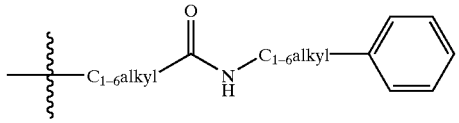

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The compounds of the present invention are thrombin or PAR-1 receptor antagonists and as such are useful in treating thrombin receptor mediated disorders, particularly PAR-1 mediated disorders including, but not limited to, inflammation, osteoporosis, hypertension, unstable angina, angina, atherosclerosis, thrombosis, restenosis, reocclusion following thrombolytic therapy, reocclusion following angioplasty, arrhythmia, myocardial infarction; heart failure, stroke, ischemic conditions, vaso-occlusive disorders, glomerulonephritis, cancer and neurodegenerative disorders. These compounds are also useful as antithrombotics in conjunction with fibrinolytic therapy (e.g., t-PA or streptokinase).

The term "subject" as used herein, refers to an animal (preferably, a mammal; most preferably, a human) who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

In the compounds of Formula (I), the amino acid residues comprising the $A_1$ and $A_2$ substituents for Y are attached to the adjacent moiety according to standard nomenclature for amino-acids (unless indicated otherwise, the amino acids bear the "L" absolute configuration). Accordingly, the amino-terminus (N-terminus) of the amino acid is drawn on the left and the carboxy-terminus of the amino acid is drawn on the right. In the figure below the carboxyl-terminus is drawn to the right and capped with an amine group.

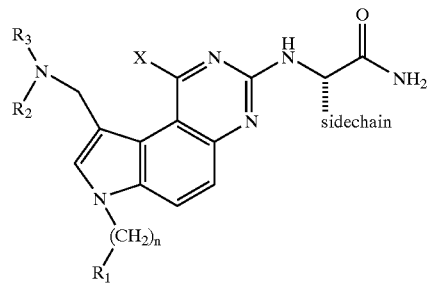

When used in the examples and throughout this application, the following amino acid abbreviations have the meanings recited hereinafter:

| | |
|---|---|
| Ala | Alanine |
| β-Ala | beta-Alanine |
| Arg | Arginine |
| hArg | homoArginine |
| Cha | Cyclohexylalanine |
| Cit | Citrulline |
| Cys | Cysteine |
| Dbu | 2,4-Diaminobutyric acid |
| Dpr | Diaminopropionic acid |
| Gln | Glutamine |
| Gly | Glycine |
| His | Histidine |
| Lys | Lysine |
| Met | Methionine |
| Nal | Naphthylalanine |
| Orn | Ornithine |
| pFPhe | paraFluorophenylalanine |
| Phe | Phenylalanine |
| hPhe | homoPhenylalanine |
| Pro | Proline |
| Pyr-Ala | Pyridylalanine |
| Ser | Serine |
| hSer | homoSerine |
| Tic | Tetrahydroisoquinoline-3-COOH |
| Tyr | Tyrosine |
| Val | Valine |

An example of the invention is a method of treating a thrombin receptor mediated disorder (preferably, a PAR-1 mediated disorder) selected from arterial and/or venous thrombosis, myocardial infarction, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, cancer, neurodegenerative disorders and a variety of vaso-occlusive disorders in a subject in need thereof comprising administering to the subject a therapeutically effective amount of any of the compounds or pharmaceutical compositions described above. In a preferred embodiment, the therapeutically effective amount of the compound is from about 0.01 mg/kg/day to about 300 mg/kg/day.

The utility of the compounds to treat PAR-1 mediated disorders (e.g., thrombin receptor mediated disorders) can be determined according to the procedures described herein. The present invention therefore provides a method of treating PAR-1 mediated disorders in a subject in need thereof which comprises administering any of the compounds as defined herein in a quantity effective to treat PAR-1 mediated disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets,* Second Edition, Revised and Expanded, Volumes 1–3, edited by Lieberman, et al.; *Pharmaceutical Dosage Forms: Parenteral Medications,* Volumes 1–2, edited by Avis, et al.; and *Pharmaceutical Dosage Forms: Disperse Systems,* Volumes 1–2, edited by Lieberman, et al.; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 300 mg (preferably, from about 0.01 mg to about 100 mg; and, more preferably, from about 0.01 mg to about 30 mg) and may be given at a dosage of from about 0.01 mg/kg/day to about 300 mg/kg/day (preferably, from about 0.01 mg/kg/day to about 100 mg/kg/day; and, more preferably, from about 0.01 mg/kg/day to about 30 mg/kg/day). Preferably, in the method for the treatment of thrombin or PAR-1 mediated disorders described in the present invention and using any of the compounds as defined herein, the dosage form will contain a pharmaceutically acceptable carrier containing between about 0.01 mg and 100 mg; and, more preferably, between about 5 mg and 50 mg of the compound; and, may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W. R. Grace/ Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c)dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxyethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of thrombin mediated disorders, particularly PAR-1 mediated disorders, is required for a subject in need thereof.

The daily dose of a pharmaceutical composition of the present invention may be varied over a wide range in the subject being dosed. Preferably, the subject is a 70 kilogram (kg) adult human, having a daily dose range of from about 0.7 mg to about 21,000 mg; preferably, the range is from about 0.7 mg to about 7,000 mg per day; and, more preferably, the range is from about 0.7 mg to about 2,100 mg per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. A therapeutically effective amount of the drug is ordinarily supplied at a dosage level of from about 0.01 mg/kg to about 300 mg/kg of body weight per day. Preferably, the range is from about 0.01 mg/kg to about 100 mg/kg of body weight per day; and, most preferably, from about 0.01 mg/kg to about 30 mg/kg of body weight per day. Advantageously, compounds of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

When used in the examples and throughout this application, the following abbreviations have the meanings recited hereinafter:

| | |
|---|---|
| Ac | Acetyl |
| ACN | Acetonitrile |
| Bzl | Benzylamide |
| Boc | t-Butoxycarbonyl |
| c-$C_3H_5$ | cyclopropanyl |
| DCC | 1,3-Dicyclohexylcarbodiimide |
| DCM | Dichloromethane |
| DIC | Diisopropylcarbodiimide |
| DIEA | Diisopropylethylamine |
| DMAP | 4-Dimethylaminopyridine |
| DMF | N,N-Dimethylformamide |
| Et | Ethyl |
| Fmoc | 9-Fluorenylmethoxycarbonyl |
| h | Hour |
| HBTU | 2-(1H-Benzotriazole-1-yl)-1,1,3,3-tetramethyluronium hexafluorophosphate |
| HOAc | Acetic acid |
| HOBT | Hydroxybenzotriazole |
| Me | Methyl |
| MeOH | Methanol |
| min | Minute |
| mL | Milliliter |
| NT | Not tested |
| rt | room temperature |
| THF | Tetrahydrofuran |
| TFA | Trifluoroacetic acid |

GENERAL SYNTHETIC EXAMPLES

Representative compounds of the present invention can be synthesized in accordance with the general synthetic method described below and are illustrated more particularly in the scheme that follow. Since the scheme is an illustration, the invention should not be construed as being limited by the chemical reactions and conditions expressed. The preparation of the various starting materials used in the schemes is well within the skill of persons versed in the art.

The following scheme describes general synthetic methods whereby intermediate and target compounds of the present invention may be prepared. Additional representative compounds of the present invention can be synthesized using the intermediates prepared in accordance with the schemes and other materials, compounds and reagents known to those skilled in the art.

Scheme A illustrates the preparation of compounds of the present invention wherein a 5-nitroindole Compound A1 was alkylated with an $R_1$—$(CH_2)_n$-halide and a base, such as cesium or potassium carbonate, in a dipolar aprotic solvent, such as DMF, to give an intermediate. The intermediate was reduced in a classical manner with, for example, iron and acetic acid or with dimethyl hydrazine and iron to give an amine Compound A2. The amine Compound A2 in a dry ether solvent, such as dioxane, was treated with trichloromethyl isocyanate, followed by phosphorus oxychloride with heating to afford a pyrroloquinazoline Compound A3. Reaction of Compound A3 with excess methanol in a halogenated solvent, such as dichloromethane, gave Compound A4. Reaction of Compound A4 with the preformed iminium salt of a dialkyl amine and formaldehyde gave an intermediate Mannich base, which was further reacted with an XH group to give Compound A5. The chloride was displaced with a YH group to give the target compound of Formula (I).

A dipeptide at the Y position may be prepared by a second coupling reaction with another amino-ester (see Example 1).

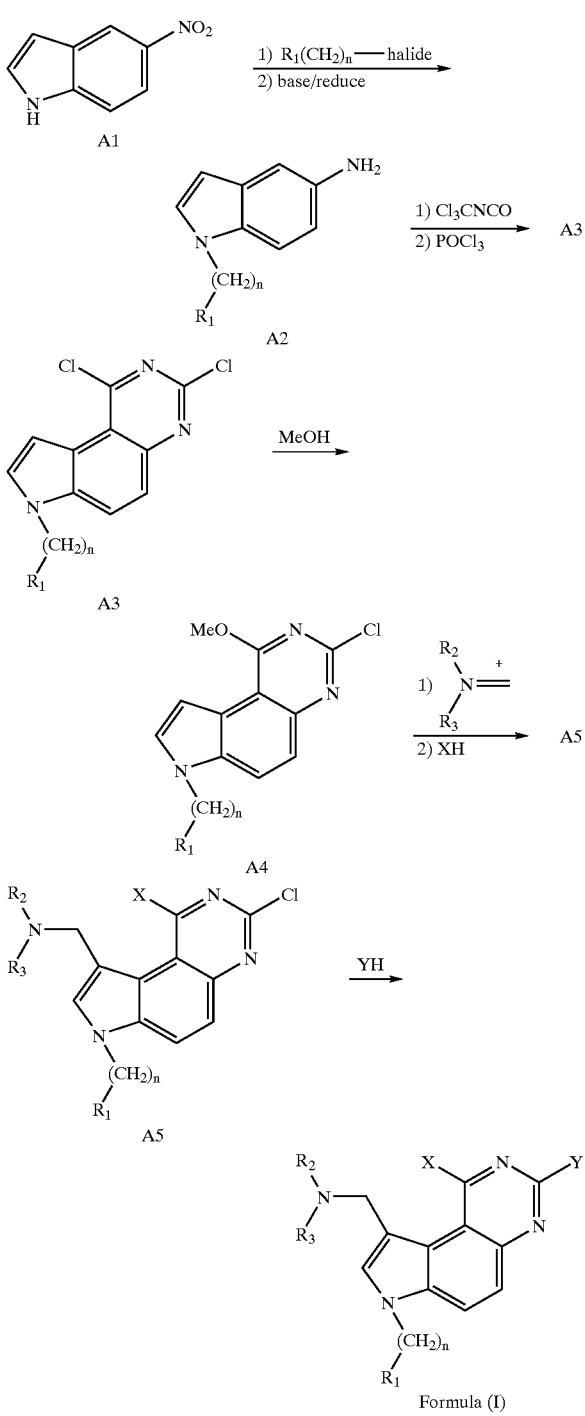

Scheme A

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Protected amino acids were purchased from Novabiochem, Bachem Bioscience, Advanced ChemTech or SyntheTech. All other chemicals were obtained from commercial suppliers and used without further purification. $^1$H and $^{13}$C NMR spectra were recorded on a Bruker AC 300B (300 MHz proton)or a Bruker AM-400 (400 MHz proton) spectrometer with Me$_4$Si as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel GF plates. Flash column chromatography was conducted with flash column silica gel (40–63 μm) and column chromatography was conducted with standard silica gel. HPLC separations were carried out on three Waters PrepPak® Cartridges (25×100 mm, Bondapak® C18, 15–20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

The following compounds were made using appropriate starting materials following the synthesis procedures set forth above except that comparative compounds 9–11 omitted step 1 of the reaction between A4 and A5.

TABLE 4

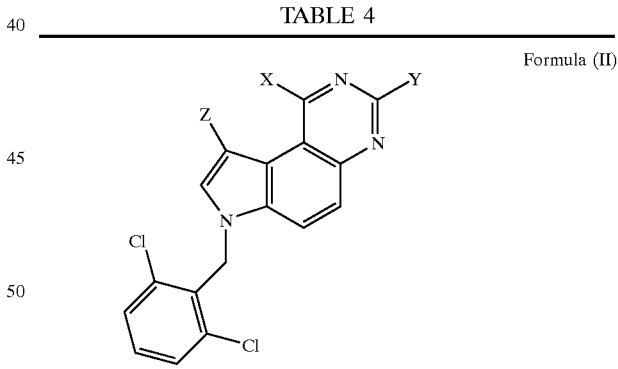

Formula (II)

wherein X, Y and Z are dependently selected from the group consisting of:

| Cpd | X | Y | Z |
|---|---|---|---|
| 1 | NH$_2$ | NH-c-C$_3$H$_5$ | N(CH$_3$)$_2$; |
| 2 | NH$_2$ | -Phe-Dbu-Bzl | N(CH$_3$)$_2$; |
| 3 | NH$_2$ | N(CH$_3$)$_2$ | N(CH$_3$)$_2$; |
| 4 | H | NH-c-C$_3$H$_5$ | N(CH$_3$)$_2$; |
| 5 | NH$_2$ | Cl | N(CH$_3$)$_4$; |
| 6 | OCH$_3$ | Cl | N(CH$_3$)$_2$; |
| 7 | NH$_2$ | Cl | N(CH$_3$)$_2$; |
| 8 | NH$_2$ | -Phe-t-butyl | N(CH$_3$)$_2$; |
| 9 | OCH$_3$ | Cl | H; |
| 10 | NH$_2$ | NH-c-C$_3$H$_5$ | H; and |
| 11 | H | Cl | H. |

Example 1

α-[[1-amino-7-[(2,6-dichlorophenyl)methyl]-9-[(dimethylamino)methyl]-7H-pyrrolo[3,2-f]quinazolin-3-yl]amino]-N-[(1S)-3-amino-1-[[(phenylmethyl)amino]carbonyl]propyl]-(α$^1$S)-benzenepropanamide (Compound 2)

A 5-Nitroindole Compound 1A (10.0 g, 62 mmol) and cesium carbonate (22 g, 67.5 mmol) were combined in DMF (70 mL) and heated to 50 C for 30 min. The solution was cooled to room temperature and 2,6-dichlorobenzyl bromide (17.3 g, 72 mmol) in DMF (40 mL) was added via addition funnel over the next 60 min and reaction stirred at rt for 20 h. The mixture was poured slowly into water (1.5 L) with vigorous stirring and stirred an additional 2 h at rt and the solid was filtered and dried in vacuo to produce an intermediate.

The intermediate (10 g, 31 mmol) was combined in MeOH (100 mL) with charcoal (1.0 g, 83 mmol), ferric chloride hexahydrate (0.54 g, 2.0 mmol) and dimethylhydrazine (21 g, 350 mmol) and refluxed for 24 h. The solution was cooled to rt, filtered through celite and the filtrate was evaporated in vacuo to an oil, which was shaken with 1N HCl (500 mL) and ether. The aqueous solid was separated and extracted again with ether (ether extracts discarded) and brought to pH>13 with 3N NaOH then was extracted with DCM (400 mL) twice. The DCM solution was washed with NaHCO$_3$, brine and dried (K$_2$CO$_3$) and evaporated in vacuo to provide Compound 1B as a solid (8.26 g, 92%). $^1$H-NMR (CDCl$_3$) δ7.6–7.4 (m, 3H), 7.2 (d, J=8.5 Hz, 1H), 6.78 (d, J=1 Hz, 1H), 6.70 (d, J=1 Hz, 1H), 6.55 (d, J=8.5 Hz, 1H), 6.11 (s, 1H), 5.42 (s, 2H). ES-MS m/z 291 (MH$^+$).

The hydrochloride salt was prepared by dissolving all of Compound 1B in ether (500 mL) and adding 1N HCl in ether (30 mmol) to precipitate out the salt, which was filtered off. This salt (4.92 g, 15 mmol) was combined with dioxane (75 mL) and stirred as trichloromethylisocyanate (2.64 g, 16.5 mmol) was added in dropwise over 5 min and the solution was stirred at rt for 20 h. The reaction was evaporated in vacuo to a solid, which was semi-dissolved in dichloroethane (75 mL) and POCl$_3$ (30 mL) was added and the reaction refluxed for 6 h. The reaction was cooled to rt and evaporated in vacuo to afford a tacky solid, which was semi-dissolved in dry DCM and evaporated in vacuo (twice) to give a brown solid crude product Compound 1C. A sample was purified by column chromatography (DCM) to give clean Compound 1C. $^1$H-NMR (CDCl$_3$) δ8.25 (d, J=8.5 Hz, 1H), 7.83 (d, J=8.5 Hz, 1H), 7.6 (d, J=2 Hz, 1H), 7.5–7.25 (m, 4H), 5.75 (s, 2H). ES-MS m/z 396 (MH$^+$).

A portion (5.6 mmol) of the crude Compound 1C was stirred in DCM (80 mL) and MeOH (20 mL) at rt for 6 h and then evaporated in vacuo to give a crude product, which was purified by column chromatography to a white solid Compound 1D (0.40 g). $^1$H-NMR (CDCl$_3$) δ8.08 (d, J=8.5 Hz, 1H), 7.71 (d, J=8.5 Hz, 1H), 7.5–7.15 (m, 5H), 5.70 (s, 2H), 4.30 (s, 3H). ES-MS m/z 392 (MH$^+$).

Compound 1D (195 mg, 0.50 mmol) in DCM (15 mL) was combined with dimethylmethyleneammonium chloride (375 mg, 4.0 mmol) in a pressure tube, stoppered and heated at 55° C. with an oilbath for 10 h. The reaction was cooled to room temperature and diluted with DCM, washed with saturated NaHCO$_3$ and brine and the solution dried (K$_2$CO$_3$) and evaporated in vacuo to a crude, white solid intermediate (180 mg). This intermediate was added to ammonia (10 mL), which had been condensed in a pressure tube at –78 C. under argon. stoppered and stirred at room temperature for 20 h. The reaction was cooled again to –78° C., the stopper removed and the ammonia allowed to evaporate out as the reaction came to room temperature, leaving a white solid Compound 1E (intermediate corresponds to Compound 7) (180 mg). ES-MS m/z 434 (MH$^+$).

A portion of Compound 1E (100 mg, 0.23 mmol) and phenylalanine t-butyl ester (530 mg, 2.4 mmol) were combined in N-methyl pyrrolidinone (2.0 mL) in a pressure tube and heated at 140 C. for 8 h. The reaction was cooled to room temperature and diluted with water (20 mL), which was decanted off. The residual oil was dissolved in DCM, dried (K$_2$CO$_3$) and evaporated in vacuo to an oil, which was purified by column chromatography (DCM:MeOH; 20:1). A portion (30 mg, 0.048 mmol) was stirred in 20% TFA in DCM (4 mL) at room temperature for 4.5 h and evaporated in vacuo to a tan solid TFA salt of Compound 1F (45 mg).

The acid Compound 1F (36 mg, 0.044 mmol) and DIEA (20 mg, 0.155 mmol) were combined in DCM (5 mL) and HOBT (7.5 mg, 0.05 mmol) and γ-Boc 2,4-diaminobutyric acid benzylamide (14 mg, 0.045 mmol) were added, followed by DIC (11.2 mg, 0.089 mmol) and the reaction was stirred at room temperature for 20 h. The solution was evaporated in vacuo to an oil, which was purified by preparative TLC to afford the Boc protected precursor of Compound 2 (15 mg). The precursor was deprotected by stirring in 30% TFA in DCM (7 mL) at room temperature for 1 h. The solution was evaporated in vacuo and the residue was dissolved in water, frozen and lyophilized to give Compound 2 as a white solid (12 mg). $^1$H-NMR (CD$_3$OD) δ7.60–6.75 (m, 16H), 5.8 (s, 2H), 4.4 (m, 4H), 3.2 (m, 2H), 2.75–2.3 (m, 8H), 2.0 (m, 2H). ES-MS m/z 752 (MH$^+$).

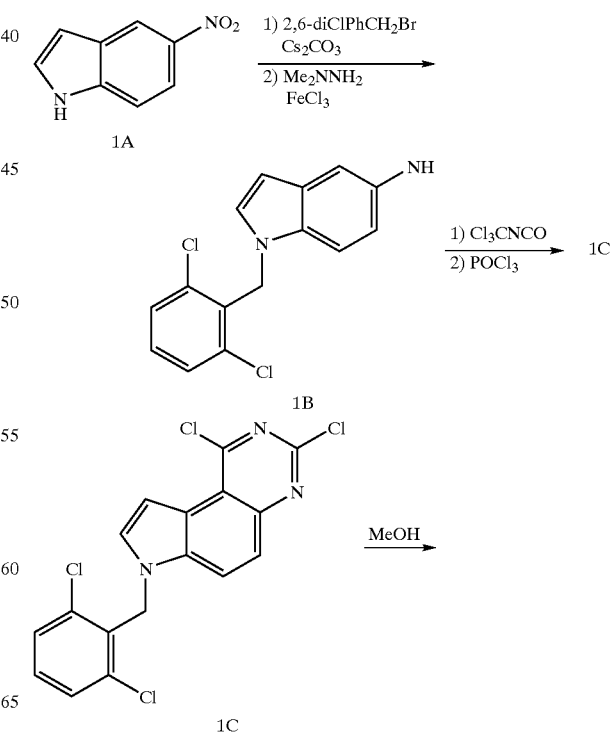

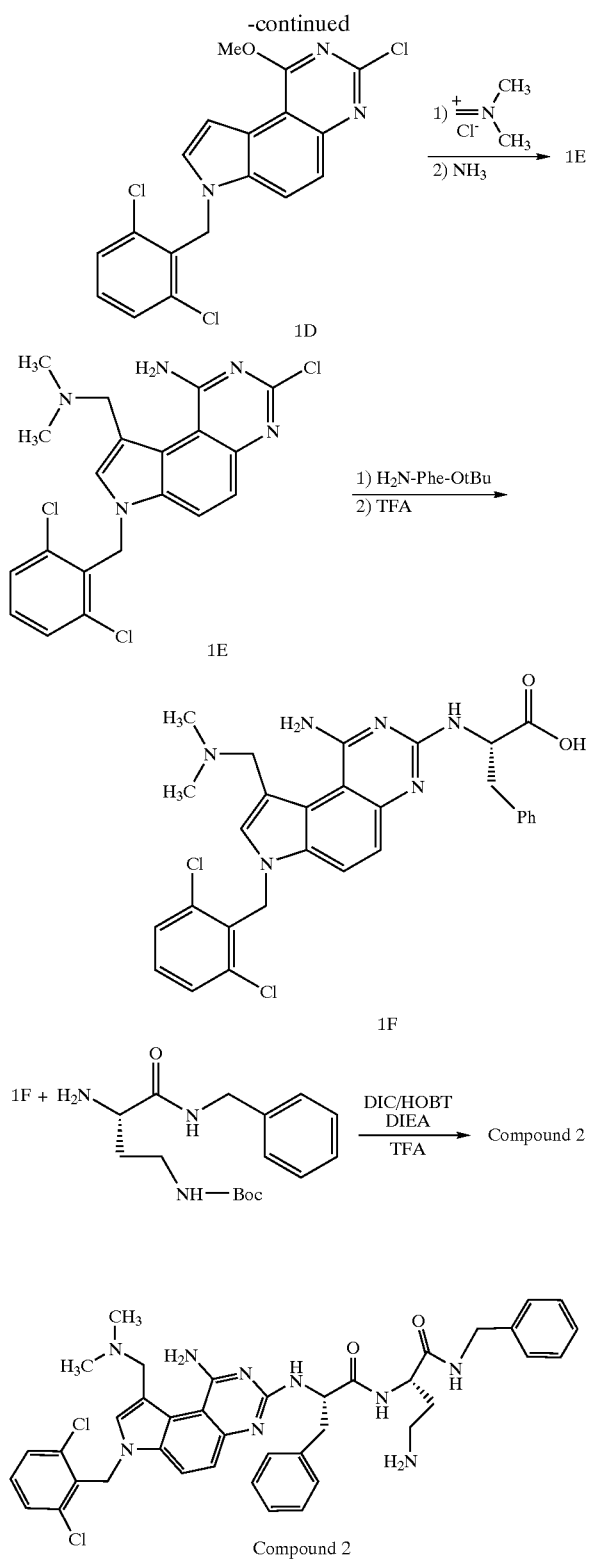

| Compound | ES-MS m/z (MH+) |
|---|---|
| 1 | 445 |
| 3 | 443 |
| 4 | 440 |
| 5 | 460 |
| 6 | 449 |
| 7 | 434 |

Example 2

As a specific embodiment of an oral composition, 100 mg of Compound 2 prepared from the method of Example 1 is formulated with sufficient finely divided lactose to provide a total amount of about 580 mg to about 590 mg to fill a size O hard gel capsule.

BIOLOGICAL EXAMPLES

The compounds of the present invention are thrombin receptor antagonists, particularly PAR-1 antagonists. The compounds interrupt platelet activation induced by thrombin's proteolytic cleavage of its platelet surface receptor, and thereby inhibit platelet aggregation. Such compounds are, therefore, useful in treating platelet-mediated thrombotic disorders (e.g., arterial and venous thrombosis, acute myocardial infarction, reocclusion following thrombolytic therapy and angioplasty, and a variety of vaso-occlusive disorders) and other PAR-1 mediated disorders.

In Vitro Thrombin Receptor Binding Assay

CHRF membranes (Jones, *Biochim. Biophys. Acta* 1992, 1136, 272) are thawed from −70° C., centrifuged at maximum speed for 5 min, washed twice with binding buffer (50 mM HEPES containing 5 mM $MgCl_2$ and 0.1% BSA), and re-suspended in binding buffer (25 μg/100 mL). 100 μL of membranes are added to the 24-Wallac plates and delivered to the Tomtech apparatus. In a typical experiment, 6 μL of samples (from a 125 μg/mL intermediary plate, 20% DMSO) and 44 μL buffer are delivered to the plates (final conc. of compounds is 3.7 μg/mL, 0.6% DMSO). Similarly, 6 μL 20% DMSO and 44 μL buffer are delivered to both column 1 (NSB) and column 12 (TB). 10 μL Ser-pFPhe-hArg-Leu-hArg-Lys-Tyr-$NH_2$ (721–40; 500 μM in deionized water) is added to column 1.50 μL tritiated 721–40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are presoaked 3 h in 0.5% polyethylenimine in HEPES/0.1M N-acetylglucosamine) are set in saran wrap and dried for 3 min in the microwave, and placed in sample bags (Wallac 1450–432). 4.5 mL scintillation fluid (Wallac, Betaplate Scint 1205–440) is added. The bags are sealed, placed in filter cassettes (Wallac 1450–104), and analyzed on the microbeta counter.

In Vitro Inhibition of Thrombin-Induced Gel-Filtered Platelet Aggregation Assay

The percentage of platelet aggregation is calculated as an increase in light transmission of compound-treated platelet concentrate vs. control-treated platelet concentrate. Human blood is obtained from drug free, normal donors in tubes containing 0.13 M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to $2 \times 10^7$ platelets per sample. The following con- Using the procedure of Example 1 and the appropriate reagents and starting materials known to those skilled in the art, other compounds of the present invention may be prepared including, but not limited to:

stituents are added to a siliconized cuvette: concentrated platelet filtrate and Tyrode's buffer (0.14 M NaCl, 0.0027 M KCl, 0.012 M $NaHCO_3$, 0.76 mM $Na_2HPO_4$, 0.0055 M glucose, 2 mg/mL BSA and 5.0 mM HEPES@pH 7.4) in an amount equal to 350 μL, 50 μL of 20 mM calcium and 50 μL of the test compound. Aggregation is monitored in a BIO-DATA aggregometer for the 3 min following the addition of agonist (thrombin 50 μL of 1 unit/mL).

Table 5 shows the biological activity of some of the compounds of the present invention. Table 5 contains $IC_{50}$ values (μM) or % inhibition@50 μM of the compounds against platelet aggregation stimulated (GFP Aggr.) by thrombin or TRAP-6 (Thr or TRAP-6) and $IC_{50}$ values (μM) in a thrombin receptor (PAR-1) binding assay (Binding). The compounds of Table 5 correspond to those shown on Table 4.

TABLE 5

| Cmpd | GFP Aggr. $IC_{50}$ (μM) or % Inhibition | | Binding $IC_{50}$ (μM) |
|---|---|---|---|
| | Thr | TRAP-6 | Thr. |
| 1 | 21 | 13 | 9.6 |
| 2 | 13 | 3 | NT |
| 3 | 27% | 40% | NT |
| 4 | 30% | 20% | NT |
| 5 | 16% | 32% | NT |
| 6 | 40% | 31 | NT |
| 7 | 14% | 3% | NT |
| 8 | −1% | −7% | NT |
| 9 | −4.5% | −2% | NT |
| 10 | 16 | 12 | NT |
| 11 | −6% | −1% | NT |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

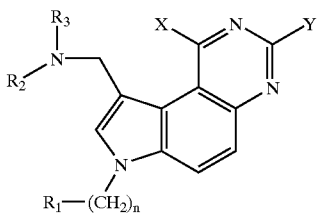

Formula (I)

wherein:

$R_1$ is selected from the group consisting of aryl, heteroaryl and $C_3$–$C_8$ cycloalkyl optionally substituted with one to five substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heteroaryl, amino, amido, amidino, guanidino, hydroxy, nitro and cyano;

$R_2$ and $R_3$ are independently selected from the group consisting of hydrogen, $C_1$–$C_8$ alkyl, $C_2$–$C_8$ alkenyl, $C_2$–$C_8$ alkynyl, $C_3$–$C_8$ cycloalkyl and aryl($C_1$–$C_8$) alkyl; alternatively, when independently selected from the group consisting of $C_1$–$C_8$ alkyl and $C_2$–$C_8$ alkenyl, $R_2$ and $R_3$ may, together with the nitrogen to which they are attached, form a saturated or partially saturated 4 to 6 membered heterocyclyl ring;

n is an integer selected from 0, 1, 2 or 3;

X is selected from the group consisting of hydrogen, —$OR_4$, —$NH_2$, —$NHR_4$ and —$NR_4R_5$;

$R_4$ and $R_5$ are independently selected from the group consisting of $C_1$–$C_8$alkyl, $C_3$–$C_8$ cycloalkyl and aryl($C_1$–$C_8$)alkyl;

Y is selected from the group consisting of halogen, —$NH_2$, —$NHR_6$, —$NR_6R_7$, —$A_1$—$NH_2$, —$A_1$—$NHR_6$, —$A_1$—$NR_6R_7$, —$A_1$—$A_2$—$NH_2$, —$A_1$—$A_2$—$NHR_6$ and —$A_1$—$A_2$—$NR_6R_7$;

$R_6$ and $R_7$ are independently selected from the group consisting of $C_1$–$C_8$alkyl, $C_3$–$C_8$ cycloalkyl and aryl($C_1$–$C_8$)alkyl; and, $A_1$ and $A_2$ are independently selected from the L-amino acid residue group consisting of arginine, homoarginine, 2,4-diaminobutyric acid, lysine, ornithine, histidine, phenylalanine, homophenylalanine, naphthylalanine, cyclohexylalanine, tryptophan and tyrosine optionally substituted with one to three substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heterocyclyl, amino, amido, amidino, guanidino, hydroxy, nitro and cyano;

and pharmaceutically acceptable salts thereof.

2. The compound of claim 1 wherein $R_1$ is selected from the group consisting of aryl and heteroaryl optionally substituted with one to five substituents independently selected from the group consisting of halogen, $C_1$–$C_4$ alkyl, $C_1$–$C_4$ alkoxy, amino, amido, amidino, guanidino, hydroxy, nitro and cyano.

3. The compound of claim 1 wherein $R_1$ is selected from aryl optionally substituted with one to five substituents independently selected from the group consisting of halogen, $C_1$–$C_4$ alkyl, $C_1$–$C_4$ alkoxy, amino, amido, amidino, guanidino, hydroxy, nitro and cyano.

4. The compound of claim 1 wherein $R_1$ is selected from phenyl substituted with two substituents independently selected from halogen.

5. The compound of claim 1 wherein $R_2$ and $R_3$ are independently selected from $C_1$–$C_4$ alkyl; alternatively, $R_2$ and $R_3$ may, together with the nitrogen to which they are attached, form a saturated 5 or 6 membered heterocyclyl ring.

6. The compound of claim 1 wherein $R_2$ and $R_3$ are independently selected from methyl, ethyl and propyl; alternatively, $R_2$ and $R_3$ may, together with the nitrogen to which they are attached, form a saturated heterocyclyl ring selected from the group consisting of pyrrolidinyl and piperidinyl.

7. The compound of claim 1 wherein $R_2$ and $R_3$ are selected from methyl; alternatively, $R_2$ and $R_3$ may, together with the nitrogen to which they are attached, form a saturated heterocyclyl ring selected from pyrrolidinyl.

8. The compound of claim 1 wherein n is 1.

9. The compound of claim 1 wherein X is selected from the group consisting of hydrogen, —$OR_4$, —$NH_2$, —$NHR_4$ and —$NR_4R_5$.

10. The compound of claim 1 wherein X is selected from the group consisting of hydrogen, —$OR_4$ and —$NH_2$.

11. The compound of claim 1 wherein X is selected from —$NH_2$.

12. The compound of claim 1 wherein $R_4$ and $R_5$ are selected from $C_1$–$C_8$alkyl.

13. The compound of claim 1 wherein $R_4$ is selected from the group consisting of methyl, ethyl and propyl.

14. The compound of claim 1 wherein $R_4$ is methyl.

15. The compound of claim 1 wherein Y is selected from the group consisting of halogen, —$NHR_6$, —$NR_6R_7$ and —$A_1$—$A_2$—$NHR_6$.

16. The compound of claim 1 wherein Y is selected from the group consisting of chlorine, —NHR₆, —NR₆R₇ and —A₁—A₂—NHR₆.

17. The compound of claim 1 wherein Y is selected from the group consisting of —NHR₆ and —A₁—A₂—NHR₆.

18. The compound of claim 1 wherein R₆ and R₇ are independently selected from the group consisting of methyl, ethyl, propyl, cyclopropyl, cyclopentyl, cyclohexyl, benzyl, phenethyl and phenylpropyl.

19. The compound of claim 1 wherein R₆ and R₇ are independently selected from the group consisting of methyl, cyclopropyl and benzyl.

20. The compound of claim 1 wherein R₆ is selected from the group consisting of cyclopropyl and benzyl.

21. The compound of claim 1 wherein A₁ and A₂ are independently selected from the L-amino acid residue group consisting of 2,4-diaminobutyric acid and phenylalanine.

22. The compound of claim 1 selected from the group consisting of:

N³-cyclopropyl-7-[(2,6-dichlorophenyl)methyl]-9-[(dimethylamino)methyl]-7H-pyrrolo[3,2f] quinazoline-1,3-diamine;

α[[1-amino-7-[(2,6-dichlorophenyl)methyl]-9-[(dimethylamino)methyl]-7H-pyrrolo[3,2-f] quinazolin-3-yl]amino]-N-[(1S)-3-amino-1-[[(phenylmethyl)amino]carbonyl]propyl]-(α¹S)-benzenepropanamide;

7-[(2,6-dichlorophenyl)methyl]-9-[(dimethylamino) methyl]-N³,N³-dimethyl-7H-pyrrolo[3,2-f] quinazoline-1,3-diamine;

3-(cyclopropylamino)-7-[(2,6-dichlorophenyl)methyl]-N,N-dimethyl-7H-pyrrolo[3,2-f]quinazoline-9-methanamine;

3-chloro-7-[(2,6-dichlorophenyl)methyl]-9-(1-pyrrolidinylmethyl)-7H-pyrrolo[3,2-f]quinazolin-1-amine;

3-chloro-7-[(2,6-dichlorophenyl)methyl]-1-methoxy-N, N-dimethyl-7H-pyrrolo[3,2-f]quinazoline-9-methanamine; and, 1-amino-3-chloro-7-[(2,6-dichlorophenyl)methyl]-N,N-dimethyl-7H-pyrrolo[3,2-f]quinazoline-9-methanamine;

and pharmaceutically acceptable salts thereof.

23. The compound of claim 1 of Formula (Ia):

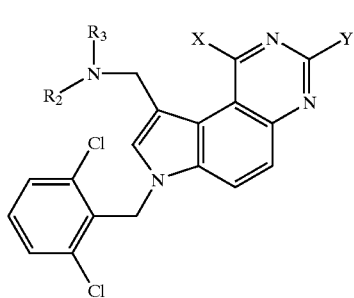

Formula (Ia)

wherein X, Y, R₂ and R₃ are dependently selected from the group consisting of:

| X | Y | R₂, R₃ |
|---|---|---|
| NH₂ | NH-c-C₃H₅ | CH₃, CH₃; |
| NH₂ | -Phe-Dbu-Bzl | CH₃, CH₃; |
| NH₂ | N(CH₃)₂ | CH₃, CH₃; |

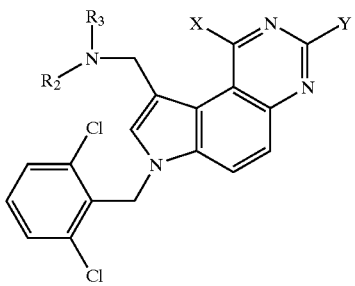

Formula (Ia)

wherein X, Y, R₂ and R₃ are dependently selected from the group consisting of:

| X | Y | R₂, R₃ |
|---|---|---|
| H | NH-c-C₃H₅ | CH₃, CH₃; |
| NH₂ | Cl | —(CH₂)₄—, |
| OCH₃ | Cl | CH₃, CH₃; and, |
| NH₂ | Cl | CH₃, CH₃; | and pharmaceutically acceptable salts thereof.

24. The compound of claim 23 of Formula (Ia) wherein X, Y, R₂ and R₃ are dependently selected from the group consisting of:

| X | Y | R₂, R₃ |
|---|---|---|
| NH₂ | NH-c-C₃H₅ | CH₃, CH₃; and, |
| NH₂ | -Phe-Dbu-Bzl | CH₃, CH₃; | and pharmaceutically acceptable salts thereof.

25. A pharmaceutical composition comprising a compound of Formula (I):

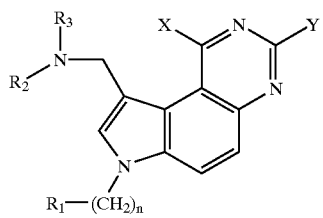

Formula (I)

wherein:

R₁ is selected from the group consisting of aryl, heteroaryl and C₃-C₈ cycloalkyl optionally substituted with one to five substituents independently selected from the group consisting of halogen, C₁-C₄ alkyl, C₂-C₄ alkenyl, C₂-C₄ alkynyl, C₁-C₄ alkoxy, aryl, heteroaryl, amino, amido, amidino, guanidino, hydroxy, nitro and cyano;

R₂ and R₁ are independently selected from the group consisting of hydrogen, C₁-C₈ alkyl, C₂-C₈ alkenyl, C₂-C₈ alkynyl, C₃-C₈ cycloalkyl and aryl(C₁-C₈) alkyl; alternatively, when independently selected from the group consisting of C₁-C₈ alkyl and C₂-C₈ alkenyl, R₂ and R₃ may, together with the nitrogen to which they are attached, form a saturated or partially saturated 4 to 6 membered heterocyclyl ring;

n is an integer selected from 0, 1, 2 or 3;

X is selected from the group consisting of hydrogen, —OR₄, —NH₂, —NHR₄ and —NR₄R₅;

$R_4$ and $R_5$ are independently selected from the group consisting of $C_1$–$C_8$alkyl, $C_3$–$C_8$ cycloalkyl and aryl($C_1$–$C_8$)alkyl;

Y is selected from the group consisting of halogen, —$NH_2$, —$NHR_6$, —$NR_6R_7$, —$A_1$—$NH_2$, —$A_1$—$NHR_6$, —$A_1$—$NR_6R_7$, —$A_1$—$A_2$—$NH_2$, —$A_1$—$A_2$—$NHR_6$ and —$A_1$—$A_2$—$NR_6R_7$;

$R_6$ and $R_7$ are independently selected from the group consisting of $C_1$–$C_8$alkyl, $C_3$–$C_8$ cycloalkyl and aryl($C_1$–$C_8$)alkyl; and, $A_1$ and $A_2$ are independently selected from the L-amino acid residue group consisting of arginine, homoarginine, 2,4-diaminobutyric acid, lysine, ornithine, histidine, phenylalanine, homophenylalanine, naphthylalanine, cyclohexylalanine, tryptophan and tyrosine optionally substituted with one to three substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heterocyclyl, amino, amido, amidino, guanidino, hydroxy, nitro and cyano;

and pharmaceutically acceptable salts thereof and a pharmaceutically acceptable carrier.

26. A method for the treatment of a thrombin mediated or PAR-1 mediated disorder wherein the disorder is selected from the group consisting of hypertension, unstable angina, angina, atherosclerosis, arterial thrombosis, venous thrombosis, restenosis, reocclusion following thrombolytic therapy, reocclusion following angioplasty, arrhythmia, myocardial infarction, acute myocardial infarction, heart failure, stroke, ischemic conditions, vaso-occlusive disorders and glomerulonephritis in a subject in need thereof comprising administering to the subject a therapeutically effective amount of a compound of Formula (I):

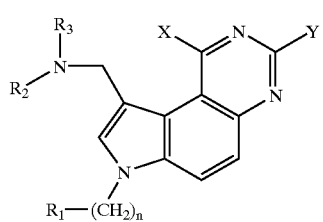

Formula (I)

wherein:

$R_1$ is selected from the group consisting of aryl, heteroaryl and $C_3$–$C_8$ cycloalkyl optionally substituted with one to five substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heteroaryl, amino, amido, amidino, guanidino, hydroxy, nitro and cyano;

$R_2$ and $R_3$ are independently selected from the group consisting of hydrogen, $C_1$–$C_8$ alkyl, $C_2$–$C_8$ alkenyl, $C_2$–$C_8$ alkynyl, $C_3$–$C_8$ cycloalkyl and aryl($C_1$–$C_8$) alkyl; alternatively, when independently selected from the group consisting of $C_1$–$C_8$ alkyl and $C_2$–$C_8$ alkenyl, $R_2$ and $R_3$ may, together with the nitrogen to which they are attached, form a saturated or partially saturated 4 to 6 membered heterocyclyl ring;

n is an integer selected from 0, 1, 2 or 3;

X is selected from the group consisting of hydrogen, —$OR_4$, —$NH_2$, —$NHR_4$ and —$NR_4R_5$;

$R_4$ and $R_5$ are independently selected from the group consisting of $C_1$–$C_8$alkyl, $C_3$–$C_8$ cycloalkyl and aryl($C_1$–$C_8$)alkyl;

Y is selected from the group consisting of halogen, —$NH_2$, —$NHR_6$, —$NR_6R_7$, —$A_1$—$NH_2$, —$A_1$—$NHR_6$, —$A_1NR_6R_7$, —$A_1$—$A_2$—$NH_2$, —$A_1$—$A_2$—$NHR_6$ and —$A_1$—$A_2$—$NR_6R_7$;

$R_6$ and $R_7$ are independently selected from the group consisting of $C_1$–$C_8$alkyl, $C_3$–$C_8$ cycloalkyl and aryl($C_1$–$C_8$)alkyl; and, $A_1$ and $A_2$ are independently selected from the L-amino acid residue group consisting of arginine, homoarginine, 2,4-diaminobutyric acid, lysine, ornithine, histidine, phenylalanine, homophenylalanine, naphthylalanine, cyclohexylalanine, tryptophan and tyrosine optionally substituted with one to three substituents independently selected from the group consisting of halogen, $C_1$–$C_4$ alkyl, $C_2$–$C_4$ alkenyl, $C_2$–$C_4$ alkynyl, $C_1$–$C_4$ alkoxy, aryl, heterocyclyl, amino, amido, amidino, guanidino, hydroxy, nitro and cyano;

and pharmaceutically acceptable salts thereof.

27. The method of claim 26 wherein the therapeutically effective amount of the compound is from about 0.01 mg/kg/day to about 300 mg/kg/day.

* * * * *